United States Patent
Choi et al.

(10) Patent No.: US 9,486,165 B2
(45) Date of Patent: Nov. 8, 2016

(54) PORTABLE LANCING DEVICE USING LASER AND EQUIPPED WITH DOUBLE SAFETY DEVICE AND DISPOSABLE CAP USED THEREWITH

(75) Inventors: Kee Jung Choi, Daejeon-si (KR); Yong Jae Heo, Daejeon-si (KR); Jung Seuk Choi, Incheon-si (KR)

(73) Assignee: ISOTECH CO., LTD. (KR)

( * ) Notice: Subject to any disclaimer, the term of this patent is extended or adjusted under 35 U.S.C. 154(b) by 96 days.

(21) Appl. No.: 14/008,105

(22) PCT Filed: Apr. 15, 2011

(86) PCT No.: PCT/KR2011/002689
§ 371 (c)(1),
(2), (4) Date: Oct. 24, 2013

(87) PCT Pub. No.: WO2012/133975
PCT Pub. Date: Oct. 4, 2012

(65) Prior Publication Data
US 2014/0039347 A1    Feb. 6, 2014

(30) Foreign Application Priority Data
Mar. 31, 2011   (KR) .......................... 10-2011-0029314

(51) Int. Cl.
*A61B 5/151*   (2006.01)
*A61B 5/15*    (2006.01)

(52) U.S. Cl.
CPC ......... *A61B 5/15138* (2013.01); *A61B 5/1411* (2013.01); *A61B 5/150022* (2013.01); *A61B 5/15113* (2013.01); *A61B 5/150259* (2013.01); *A61B 5/150954* (2013.01)

(58) Field of Classification Search
CPC ............ A61B 5/14532; A61B 5/1411; A61B 5/1455
See application file for complete search history.

(56) References Cited

U.S. PATENT DOCUMENTS

| | | | | |
|---|---|---|---|---|
| 4,608,997 | A  * | 9/1986  | Conway | 600/576 |
| 2002/0058953 | A1 | 5/2002  | Gruzdev et al. | |
| 2002/0173732 | A1* | 11/2002 | Hakky et al. | 600/573 |
| 2004/0220495 | A1 | 11/2004 | Cahir et al. | |
| 2010/0030110 | A1* | 2/2010  | Choi et al. | 600/583 |

(Continued)

FOREIGN PATENT DOCUMENTS

| | | |
|---|---|---|
| CN | 1553787 | 12/2004 |
| EP | 2153792 | 2/2010 |

(Continued)

OTHER PUBLICATIONS

European Search Report—European Application No. 11862322.2 issued on Aug. 22, 2014, citing EP2153792, U52009/191147, WO2008/054812, US2002/058953, WO02/26148 and US2004/220495.

(Continued)

*Primary Examiner* — Adam J Eiseman
*Assistant Examiner* — Patrick Fernandes
(74) *Attorney, Agent, or Firm* — Cantor Colburn LLP (57) ABSTRACT

A portable laser blood sampling device equipped with a dual safety device and a disposable cap used therewith are provided. Specifically, a portable laser blood sampling device equipped with a dual safety device which enables safe laser irradiation when a laser is irradiated to the outside by a laser module and a disposable cap used therewith are provided.

10 Claims, 6 Drawing Sheets

(56) References Cited

U.S. PATENT DOCUMENTS

2010/0191147 A1 7/2010 Miyoshi et al.
2011/0166478 A1 7/2011 Choi

FOREIGN PATENT DOCUMENTS

| | | |
|---|---|---|
| JP | 2010094165 | 4/2010 |
| KR | 1020100025086 | 3/2010 |
| KR | 1020100085224 | 7/2010 |
| TW | 200911317 | 3/2009 |
| WO | 0226148 | 4/2002 |
| WO | 2008054812 | 5/2008 |

OTHER PUBLICATIONS

International Search Report—PCT/KR2011/002689 dated Feb. 15, 2012.

* cited by examiner

PORTABLE LANCING DEVICE USING LASER AND EQUIPPED WITH DOUBLE SAFETY DEVICE AND DISPOSABLE CAP USED THEREWITH

TECHNICAL FIELD

The present invention relates to a portable laser blood sampling device equipped with a dual safety device, which draws a small amount of blood by stimulating a capillary vessel under the skin using an Er:YAG laser, and a disposable cap used therewith.

BACKGROUND ART

In general, an Er:YAG laser generating device used for painless blood sampling includes a reflector formed by depositing or plating a surface of a metal body with silver, nickel, copper, or an alloy thereof several times and performing a surface process to the resultant structure. The reflector is equipped with a flash lamp and an Er:YAG crystal rod for generating a laser therein.

Further, an output intensity of a laser emitted from the Er:YAG laser generating device varies depending on the light emitting amounts of a photocapacitor and the flash lamp, which determine an input voltage of the flash lamp, and the volume, length, and density of the Er:YAG crystal rod.

A laser blood sampling device including a laser module configured as described above may cause a fatal problem to a user in a general situation or when the laser module malfunctions.

Therefore, in order to provide the laser blood sampling device for a user's convenience, a size of the laser blood sampling device needs to be reduced so as to be used for a diabetic who draws his/her blood several times a day. However, even if a size of the laser module is reduced, various safety devices need to be provided on the outside of the laser blood sampling device to suppress of malfunction of the laser module. Therefore, the laser blood sampling device cannot be substantially miniaturized.

Furthermore, if the laser blood sampling device includes a focus lens which collects lasers irradiated from the laser module, when a laser generated by the laser module is irradiated to a user's target point, foreign substances such as dust or smoke may be generated.

DISCLOSURE OF THE INVENTION

Problems to be Solved by the Invention

Accordingly, a technical problem to be solved by the present invention is to provide a laser blood sampling device miniaturized to be portable and equipped with a dual safety device to suppress malfunction of a laser module.

Further, another technical problem to be solved by the present invention is to provide an optical window or a disposable cap to protect a focus lens which collects lasers irradiated from the laser module.

Means for Solving the Problems

According to an aspect of an exemplary embodiment, a portable laser blood sampling device equipped with a dual safety device is provided. The device may include a laser module configured to generate a laser and irradiate the laser in one direction, a skin contact part that is arranged in an irradiation direction of the laser to be locally concentrated on a point of the skin to be perforated, an irradiation port cover configured to prevent the laser module from outputting the laser to the outside, a first safety switch configured to be turned on/off by up and down movements of the irradiation port cover, a second safety switch configured to be turned on/off by push and pull movements of the skin contact part by means of an elastic member between the laser module and the skin contact part and a button switch configured to allow the laser to be irradiated when both the first safety switch and the second safety switch are turned on.

In the portable laser blood sampling device equipped with a dual safety device, the skin contact part may include a disposable cap insertion port that is formed coaxially with the irradiation port cover so that a disposable cap is inserted into the disposable cap insertion port and an optical window insertion port configured to allow an optical window to be inserted into the optical window insertion port. The optical window is configured to protect a focus lens of the laser module from a foreign substance generated by an irradiation from the laser module.

In the portable laser blood sampling device equipped with a dual safety device, the optical window may be fixed at the optical window insertion port or detachably provided to the optical window insertion port.

In the portable laser blood sampling device equipped with a dual safety device, the device may further include a laser intensity control button configured to adjust an irradiation intensity of the laser module and a battery gauge configured to display a remaining battery capacity that enables operation of the laser module.

In the portable laser blood sampling device equipped with a dual safety device, the skin contact part may include a push part that elastically turns on and off the second safety switch.

According to an aspect of another exemplary embodiment, a disposable cap used with the laser blood sampling device is provided. The disposable cap may include a coupling part configured to be coupled with a disposable cap insertion port of a skin contact part, a through hole having a hollow opening in the coupling part to allow a laser to be irradiated to the outside and a handle configured to couple the coupling part to a fixing part.

In the disposable cap, one side of the through hole may include a transparent interface film that suppresses the laser blood sampling device from being contaminated from blood of a user and a lens that is provided between the transparent interface film and a user contact surface and configured to focus a laser on an external blood sampling point on a skin.

In the disposable cap, the handle may include a non-slip part that suppresses a user from slipping when the user separates the coupling part from the skin contact part.

In the disposable cap, the through hole may have a hollow cylinder shape and may be formed so as to be perpendicular to the coupling part.

Effect of the Invention

In accordance with the exemplary embodiments of the present invention,

Since the irradiation port cover or the dual safety switch parts are provided within the case section, it is possible to suppress a malfunction where a laser is irradiated to the outside while the laser blood sampling device is not in contact with a target position of the skin.

Further, since the safety devices previously provided on the outside of the laser blood sampling device are removed and instead placed inside the case, it is possible to miniaturize the laser blood sampling device.

Furthermore, since the disposable cap may have a lens depending on whether or not the laser module includes the focus lens, it is possible to improve irradiation efficiency of a laser.

[Explanation of Codes]

| | |
|---|---|
| 110: Skin contact part | 111: Irradiation port cover |
| 112: Elastic member | 113: Push part |
| 114: Optical window insertion port | 115: Disposable cap insertion port |
| 120: Laser module | 130: first safety switch |
| 140: second safety switch | 150: Capacitor |
| 160: Battery | 170: Button switch |
| 190: Battery gauge | 180: laser intensity control button |
| 200: Disposable cap | 210: Coupling part |
| 220: Through hole | 230: Handle |
| 240: Contact surface | 250: Transparent interface film |
| 260: Lens | 270: Non-slip part |
| 300: Optical window | |

BEST MODE FOR CARRYING OUT THE INVENTION

Hereinafter, exemplary embodiments of the present invention will be described in detail with reference to the accompanying drawings.

Figure 1:
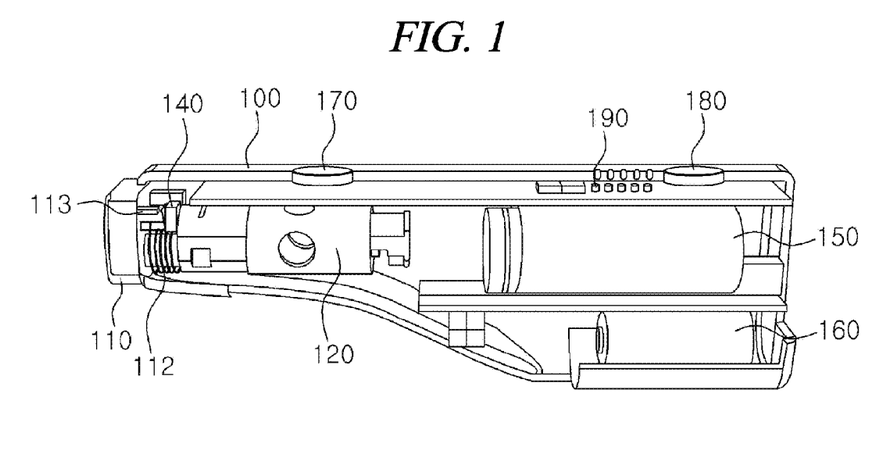
FIG. 1 provides a perspective view of a portable laser blood sampling device equipped with a dual safety device in accordance with an exemplary embodiment.
Figure 2:
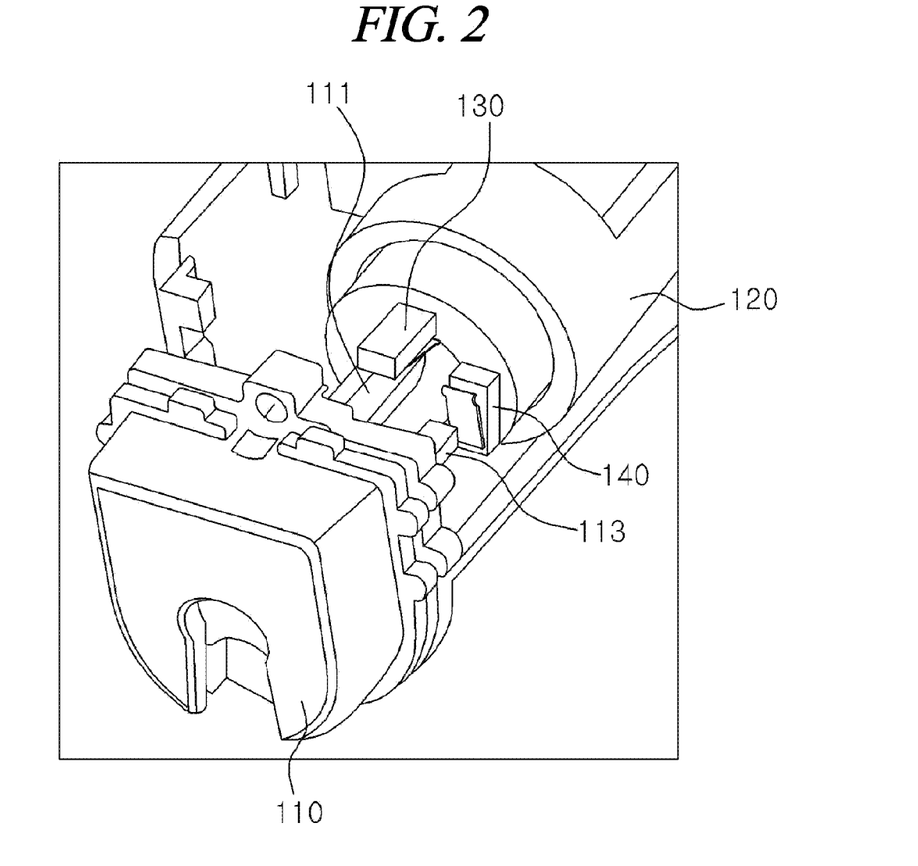
FIG. 2 provides a perspective view of a first safety switch and a second safety switch of a portable laser blood sampling device equipped with a dual safety device in accordance with an exemplary embodiment.
Figure 3:
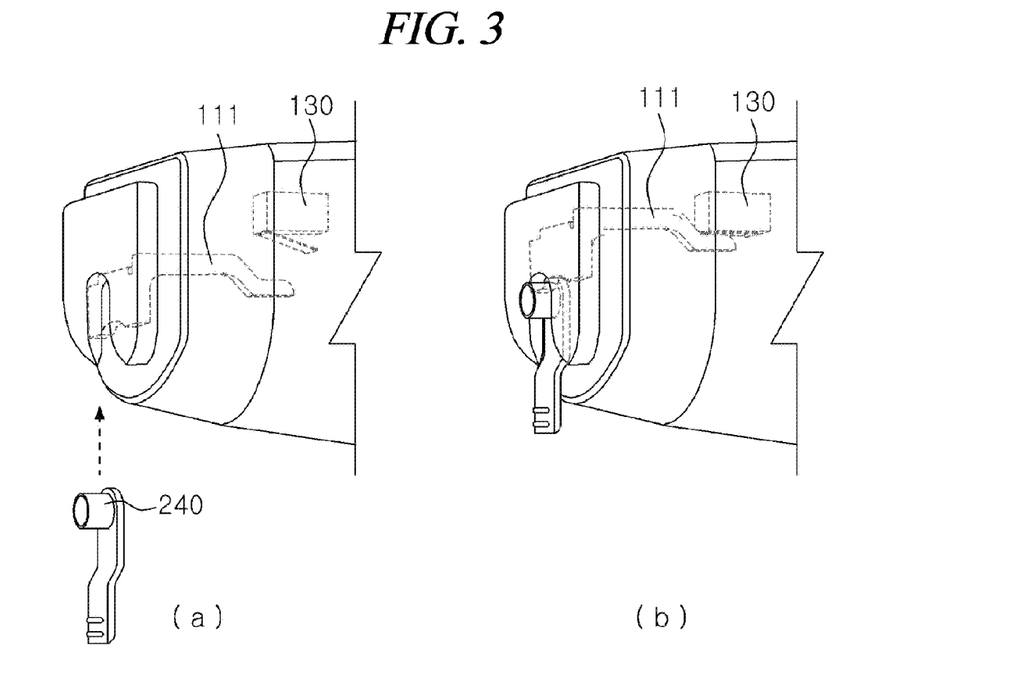
FIG. 3 provides perspective views of a portable laser blood sampling device equipped with a dual safety device and a disposable cap coupled therewith in accordance with an exemplary embodiment.
Figure 4:
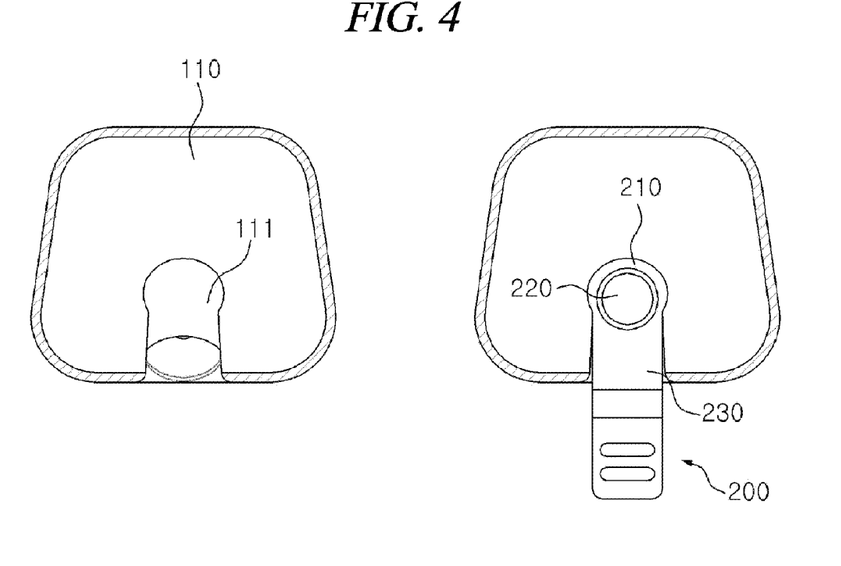
FIG. 4 provides front views of an irradiation port cover of a portable laser blood sampling device equipped with a dual safety device in accordance with an exemplary embodiment.
Figure 5:
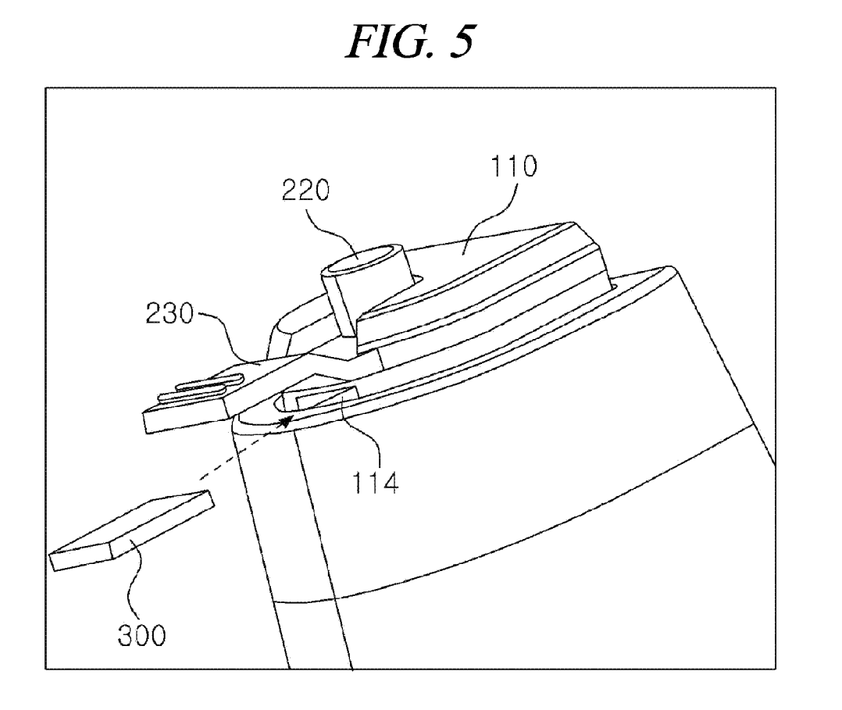
FIG. 5 provides a bottom perspective view of a skin contact part of a portable laser blood sampling device equipped with a dual safety device in accordance with an exemplary embodiment.

FIG. 1 provides a perspective view of a portable laser blood sampling device equipped with a dual safety device in accordance with an exemplary embodiment, FIG. 2 provides a perspective view of a first safety switch and a second safety switch of a portable laser blood sampling device equipped with a dual safety device in accordance with an exemplary embodiment, FIG. 3 provides perspective views of a portable laser blood sampling device equipped with a dual safety device and a disposable cap coupled therewith in accordance with an exemplary embodiment, FIG. 4 provides front views of an irradiation port cover of a portable laser blood sampling device equipped with a dual safety device in accordance with an exemplary embodiment, FIG. 5 provides a bottom perspective view of a skin contact part of a portable laser blood sampling device equipped with a dual safety device in accordance with an exemplary embodiment.

As depicted in FIG. 1 to FIG. 5, a portable laser blood sampling device equipped with a dual safety device in accordance with an exemplary embodiment of the present invention includes a skin contact part 110, a laser module 120, a first safety switch 130, a second safety switch 140, a button switch 170, laser intensity control button 180, and a battery gauge 190.

The laser module 120, the first safety switch 130, and the second safety switch 140 are arranged within a case section 100. The button switch 170, laser intensity control button 180, and the battery gauge 190 are provided on the outside of the case section 100 which a user can easily touch.

Further, the skin contact part 110 is positioned at a front surface of the case section in an irradiation direction of a laser irradiated from the laser module 120 and has elasticity due to an elastic member 112 between the case section 110 and the skin contact part 110.

Therefore, even if a user pushes the skin contact part 110 toward the case section 100, when the user does not touch the skin contact part 110 any longer, the elastic member 112 returns the skin contact part 110 to its original position.

Hereinafter, a configuration of the portable laser blood sampling device equipped with a dual safety device in accordance with an exemplary embodiment of the present invention will be explained.

The laser module 120 is a device which generates a laser and irradiates it in one direction. The laser module 120 will be explained in brief.

Herein, the laser module 120 includes a reflector, an Er:YAG crystal rod inserted into the reflector and exposed to the outside, a flash lamp, and a metal guide and a silicon guide used to fix the Er:YAG crystal rod and the flash lamp in an inner space of the reflector and absorb external impacts.

Both ends of the Er:YAG crystal rod and the flash lamp support components, which generate an Er:YAG laser, in a front part fixing cover and a rear part fixing cover respectively provided at both sides of a front end and a rear end of the reflector. There are provided a coupling which connects and fixes the front part fixing cover and the rear part fixing cover, a focusing lens which accurately focuses a laser on an external blood sampling point on a skin, and a lens bushing which fixes the focusing lens.

Further, a transflective mirror is attached to a front surface of the Er:YAG crystal rod and a total internal reflection mirror is attached to a rear surface of the Er:YAG crystal rod.

The Er:YAG crystal rod guides and concentrates a flashlight emitted from the flash lamp so as to irradiate a hydrophilic laser having an intensity of 50 mJ to 350 mJ and a wavelength of 2.94 μm to the skin. The intensity of the laser is determined depending on the crystalline structure, density, and volume of the Er:YAG crystal rod, the light emitting amount of the flash lamp, and the charge voltage and capacity of a photo capacitor 150 which determines an output of the flash lamp.

The reflector in which the Er:YAG crystal rod and the flash lamp are provided at a predetermined distance from each other is a component that forms the appearance of an Er:YAG laser generating unit. The inner surface of the reflector reflects at least 90% or more of a flashlight generated from the flash lamp and guides and concentrates the flash light to the Er:YAG crystal rod.

The laser module 120 configured as described above generates a laser and irradiates the laser in one direction, which enables a user to draw a blood sample from a finger. The laser generated by the laser module 120 is a laser having a wavelength of 2.94 μm, which enables painless blood sampling from the skin using an Er:YAG laser technology and causes substantially no harm to humans due to high absorptivity to water.

Although an exemplary embodiment using the Er:YAG laser technology has been explained, the present invention is not limited thereto. Any technology which is harmless to humans and has characteristics similar to those of the Er:YAG laser technology can be used.

The skin contact part 110 is provided in the irradiation direction so that the laser can be locally concentrated on a point of the skin to be perforated.

Herein, the skin contact part 110 includes a disposable cap insertion port 115, an irradiation port cover 111, a push part 113, and an optical window insertion port 114.

The disposable cap insertion port 115 is formed coaxially with the irradiation port cover 111 so that a disposable cap 200 can be inserted thereinto, and forms a guide which allows the disposable cap 200 to be inserted so that a through hole 220 of the disposable cap 200 and a irradiation direction of the laser module 120 are arranged collinearly.

The irradiation port cover 111 obstructs the irradiation direction of the laser module 120 through the disposable cap insertion port 115 and can be moved up and down by the disposable cap 200 inserted into the disposable cap insertion port 115. The irradiation port cover 111 is further extended into the skin contact part 110.

The push part 113 is extended inside the skin contact part 110 so as to be coaxial with the case section 100 and controls the second safety switch 140.

The optical window insertion port 114 allows an optical window 300 to be inserted thereinto. The optical window 300 is configured to block splashing of impurities such as fine drops of blood, which are generated when a blood sample is drawn using a laser irradiated from the laser module 120, onto a focusing lens (not illustrate) of the laser module 120 provided within the case section 100.

Herein, the optical window 300 may be provided integrally with the portable laser blood sampling device or may be detachably provided. If the optical window 300 is detachably provided, an additional component for attaching and detaching the optical window 300 may be provided.

Further, a material of the optical window 300 may include glass, plastic, and transparent materials which do not cause noise when a laser is transmitted to the outside.

The first safety switch 130 is a primary unlocking device which allows the laser module 120 to operate and is turned on/off by up and down movements of the irradiation port cover 111 further extended into the skin contact part 110.

That is, a switch of the first safety switch 130 is provided at an upper end of the irradiation port cover 111, and the irradiation port cover 111 touches the switch of the first safety switch 130 while moving upward.

Herein, in accordance with an exemplary embodiment of the present invention, if the irradiation port cover 111, which moves to open the irradiation direction of the laser, moves upward, the first safety switch 130 may be desirably positioned at the upper end of the irradiation port cover 111 extended into the skin contact part 110.

Meanwhile, if the irradiation port cover 111, which moves to open the irradiation direction of the laser, moves downward, the first safety switch 130 may be desirably positioned at the lower end of the irradiation port cover 111 extended into the skin contact part 110.

The second safety switch 140 is a secondary unlocking device which allows the laser module 120 to operate and is turned on/off by push and pull movements of the push part 113 extended inside the skin contact part 110 so as to be coaxial with the case section 100.

That is, by pushing the skin contact part 110 elastically connected to the laser module 120 through the elastic member 112, the second safety switch 140 is unlocked.

Further, a state where the skin contact part 110 is not pushed and is not in contact with the user is referred to as a pulled state.

The button switch 170 allows the laser module to operate so that a laser is irradiated to the outside. The button switch 170 can operated in a state where both the first safety switch 130 and the second safety switch 140 are unlocked.

That is, if any one of the first safety switch 130 and the second safety switch 140 is not unlocked (turned on), it is impossible to operate the laser module 120 with the button switch 170.

Therefore, it is possible to reduce the risk caused by malfunction of the laser module 120.

The laser intensity control button 180 is configured to adjust an irradiation intensity of the laser module 120. Since a skin thickness varies depending on a user, laser intensity is adjusted to be suitable to each user.

The battery gauge 190 displays a remaining battery capacity that enables operation of the laser module.

In accordance with the exemplary embodiment of the present invention relating to the portable laser blood sampling device, a remaining battery capacity can be checked so that the laser blood sampling device can be used at any place.

Figure 6:
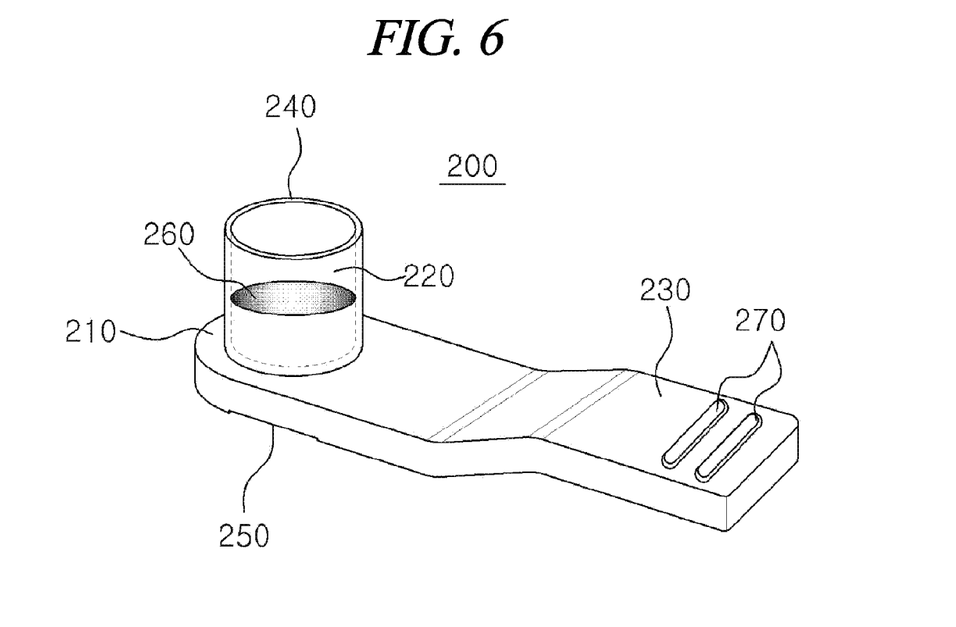
FIG. 6 provides a perspective view of a disposable cap used with a laser blood sampling device in accordance with an exemplary embodiment.
Figure 7:
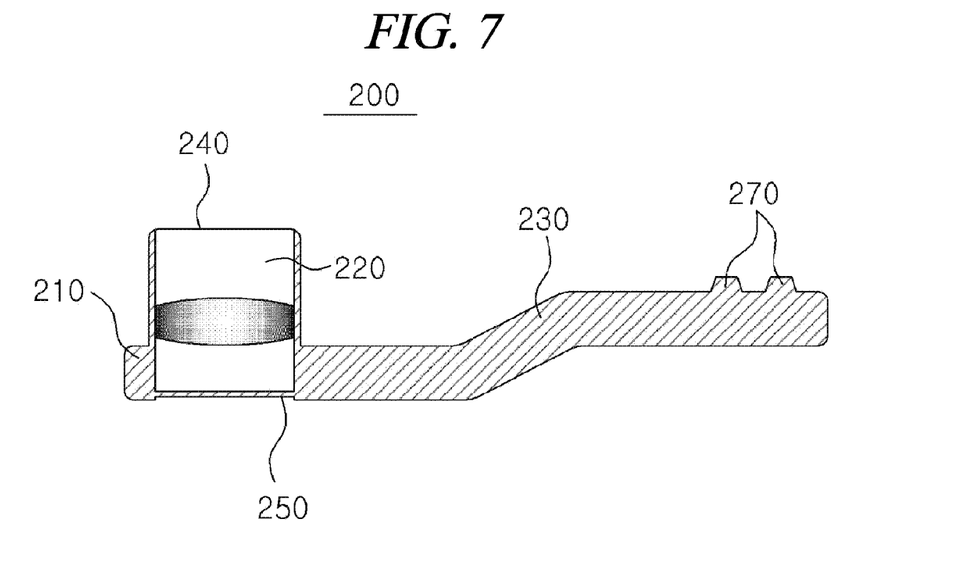
FIG. 7 provides a cross-sectional view of a disposable cap used with a laser blood sampling device in accordance with an exemplary embodiment.

FIG. 6 provides a perspective view of a disposable cap used with a laser blood sampling device in accordance with an exemplary embodiment, and FIG. 7 provides a cross-sectional view of a disposable cap used with a laser blood sampling device in accordance with an exemplary embodiment.

As depicted in FIG. 6 and FIG. 7, the disposable cap 200 used with the portable laser blood sampling device in accordance with the present invention includes a coupling part 210, a through hole 220, a handle 230, and a lens 260.

The coupling part 210 has a configuration by which the disposable cap 200 is fixed to the skin contact part 110 of the portable laser blood sampling device. The coupling part 210 may have any configuration that does not obstruct a laser irradiated from the laser blood sampling device.

The through hole 220 is comprised of a contact surface 240 which comes into contact with the user's skin to which a laser is irradiated when the laser generated by the laser module 120 is irradiated to the outside and a transparent interface film 250 which suppresses the portable laser blood sampling device from being contaminated by the blood of the user. The through hole 220 has a hollow cylinder shape with open ends and is formed so as to be perpendicular to the coupling part 210.

Herein, the transparent interface film 250 suppresses dispersion of blood or smoke which may occur when a blood sample is drawn, suppresses the focusing lens from being contaminated, and overcomes a problem of cross-infection between users caused by reuse.

Although the through hole has been illustrated as having a cylinder shape in the exemplary embodiment, such a shape is a structure that allows a laser to be efficiently irradiated to the outside, but the present invention is not limited thereto.

The handle 230 is formed integrally with the coupling part 210 so that the user can couple the coupling part 210 to the skin contact part 110 by holding the handle 230.

Herein, desirably, the handle 230 may further include a non-slip part 270 so that the user does not fumble the disposable cap 200 when the user couples or separates the coupling part 210 to or from the disposable cap insertion port 115 of the skin contact part 110.

Although a portion between the handle 230 and the coupling part 210 is inclined at a certain angle in accordance with the exemplary embodiment of the present invention, this is an ergonomic structure that facilitates coupling of the coupling part 210 to the disposable cap insertion port 115 of the skin contact part 110, but the present invention is not limited to such a structure with an angle.

The lens 260 is provided between the transparent interface film 250 and the contact surface and configured to focus a laser irradiated on the skin from which a blood sample is drawn.

Herein, if the lens 260 includes a focus lens coupled to the portable laser blood sampling device, the disposable cap 200 may not include the lens 260.

This is because if both the focus lens and the lens 260 of the disposable cap 200 are provided, efficiency of a laser passing through the two lenses may decrease.

There will be explained a process of mounting the disposable cap 200 configured as described above and a route of a laser.

The user holds the handle 230 and couples the coupling part 210 to the disposable cap insertion port 115 of the skin contact part 110.

If the disposable cap 200 is coupled to the disposable cap insertion port 115, the laser module 120 generates a laser and irradiates it to the outside. The laser passes through the transparent interface film 250 and is focused by the lens 240 so as to come into contact with the user's skin.

Therefore, when the disposable cap 200 is in contact with the user's target point, a distance between the target point and the laser module can be reduced. Thus, it is possible to remove smell, smoke, and noise which may occur when the skin is perforated.

There will be explained a sequence of an operation of the portable laser blood sampling device equipped with a dual safety device as configured as described above.

First, the disposable cap 200 is fitted into the disposable cap insertion port 115 while pushing the irradiation port cover 111 upward, and the through hole 220 of the disposable cap 200 is arranged coaxially with the irradiation direction of a laser irradiated from the laser module 120.

Then, the disposable cap 200 pushes the irradiation port cover 111 so that the irradiation port cover 111 extended into the skin contact part 110 unlocks the first safety switch 130 inside the case section 100 while moving upward.

Thereafter, a residual battery charge is checked by using the battery gauge 190 to determine whether or not the laser module 120 can operate, and an irradiation intensity of the laser module is adjusted by using the laser intensity control button 180.

Then, a target point on the skin of the user, i.e. a finger from which a blood sample is drawn, is brought into contact with the contact surface 240 of the disposable cap 200 and pushes the skin contact part 110.

In this case, the push part 113 extended inside the skin contact part 110 so as to be coaxial with the case section 100 presses and unlocks the second safety switch 140.

Finally, when both the first and second safety switches 130 and 140 are unlocked as described above, the button switch 170 is used to operate the laser module 120.

As explained above, the exemplary embodiments of the present invention have been explained in the detailed description of the present invention. However, it is apparent to those skilled in the art that various modifications and changes can be made without departing from the scope of the present invention. Therefore, it is to be understood that the scope of the present invention is not limited to the foregoing exemplary embodiments but shall be defined by the accompanying claims and their equivalents.

What is claimed is:

1. A portable laser blood sampling device equipped with a dual safety device, the device comprising:
    a laser module configured to generate a laser and irradiate the laser in one direction;
    a skin contact part that is arranged in an irradiation direction of the laser to be locally concentrated on a point of the skin to be perforated, the skin contact part including a disposable cap insertion port;
    a disposable cap having a focus lens for focusing the laser, the disposable cap configured to be inserted into the disposable cap insertion port in an intersecting direction with the irradiation direction of the laser;
    an irradiation port cover configured to prevent the laser module from outputting the laser to the outside;
    a first safety switch configured to be turned on/off by up and down movements of the irradiation port cover that is moved by up and down movements of the disposable cap;
    a second safety switch configured to be turned on/off by an elastic member provided between the laser module and the skin contact part and moved by push and pull movements of the skin contact part; and
    a button switch configured to allow the laser to be irradiated when both the first safety switch and the second safety switch are turned on.

2. The device of claim 1, wherein the skin contact part further comprises:
    an optical window insertion port configured to allow an optical window to be inserted into the optical window insertion port, the optical window configured to protect the focus lens of the laser module from a foreign substance generated by an irradiation from the laser module.

3. The device of claim 2, wherein the optical window is fixed at the optical window insertion port or detachably provided to the optical window insertion port.

4. The device of claim 1, further comprising: a laser intensity control button configured to adjust an irradiation intensity of the laser module; and a battery gauge configured to display a remaining battery capacity that enables operation of the laser module.

5. The device of claim 1, wherein the skin contact part comprises a push part that elastically turns on and off the second safety switch.

6. The device of claim 1, wherein the disposable cap comprises:
    a coupling part configured to be coupled with a disposable cap insertion port of a skin contact part;
    a through hole having a hollow opening in the coupling part to allow a laser to be irradiated to the outside; and
    a handle configured to couple the coupling part to a fixing part.

7. The device of claim 6, wherein one side of the through hole comprises:

a transparent interface film that suppresses the laser blood sampling device from being contaminated from blood of a user; and the lens is provided between the transparent interface film and a user contact surface and configured to focus a laser on an external blood sampling point on a skin.

8. The device of claim 6, wherein the handle comprises a non-slip part that suppresses a user from slipping when the user separates the coupling part from the skin contact part.

9. The device of claim 6, wherein the through hole has a hollow cylinder shape and is formed so as to be perpendicular to the coupling part.

10. The device of claim 2, further comprising:
a laser intensity control button configured to adjust an irradiation intensity of the laser module; and
a battery gauge configured to display a remaining battery capacity that enables operation of the laser module.

* * * * *